(12) United States Patent  (10) Patent No.: US 8,966,685 B2
Graw et al.  (45) Date of Patent: Mar. 3, 2015

(54) FLEXIBLE BARIATRIC OVERLAY (75) Inventors: Ansgar Graw, Chicago, IL (US); Way Moy, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 249 days.

(21) Appl. No.: 13/343,138

(22) Filed: Jan. 4, 2012

(65) Prior Publication Data

US 2013/0025054 A1 Jan. 31, 2013

Related U.S. Application Data (60) Provisional application No. 61/511,574, filed on Jul. 26, 2011.

(51) Int. Cl.
*A61G 13/00* (2006.01)
*A61G 7/10* (2006.01)
*A61G 13/12* (2006.01)
*A61B 6/04* (2006.01)
*A61B 6/03* (2006.01)

(52) U.S. Cl.
CPC .......... *A61G 7/1021* (2013.01); *A61G 13/1265* (2013.01); *A61B 6/0407* (2013.01); *A61G 7/1025* (2013.01); *A61G 2200/16* (2013.01); *A61G 2210/50* (2013.01); *A61B 6/03* (2013.01)
USPC ....... 5/601; 5/83.1; 5/81.1 R; 5/600; 128/857

(58) Field of Classification Search
USPC ........ 5/601, 81.1 R, 81.1 HS, 620, 83.1, 600; 128/857
See application file for complete search history.

(56) References Cited

U.S. PATENT DOCUMENTS

| | | | |
|---|---|---|---|
| 4,484,571 A * | 11/1984 | Velazquez | 5/601 |
| 4,935,968 A | 6/1990 | Hunt et al. | |
| 4,949,409 A | 8/1990 | Stefano | |
| 5,462,519 A | 10/1995 | Carver | |
| 6,073,291 A | 6/2000 | Davis | |
| 2007/0124858 A1* | 6/2007 | Ahlman | 5/81.1 R |
| 2007/0294823 A1 | 12/2007 | Hay | |
| 2008/0011989 A1 | 1/2008 | Davis | |
| 2008/0301873 A1 | 12/2008 | White et al. | |
| 2009/0045383 A1 | 2/2009 | King et al. | |
| 2009/0083907 A1 | 4/2009 | Ahlman | |
| 2009/0094745 A1* | 4/2009 | Benzo et al. | 5/608 |
| 2009/0158524 A1 | 6/2009 | Patterson et al. | |
| 2010/0229310 A1* | 9/2010 | Howell et al. | 5/689 |
| 2011/0092792 A1* | 4/2011 | Birman | 600/407 |

* cited by examiner

*Primary Examiner* — Peter M Cuomo
*Assistant Examiner* — Brittany Wilson
(74) *Attorney, Agent, or Firm* — Peter Kendall (57) ABSTRACT

Apparatuses for assisting patient movement to/from a gurney to/from a patient handling system are provided. In one embodiment, a bariatric overlay is provided that includes a flexible top pallet and a rigid bottom pallet. A bladder resides between the flexible top pallet and the rigid bottom pallet. When actuated, the bladder expands and props up the flexible top pallet. The flexible top pallet, rigid bottom pallet, and bladder are made of a material translucent to an imaging modality. In various embodiments, the shape of the rigid bottom pallet is similar to the shape of a scanning bed of the patient handling system. For example, when the shape of the scanning bed is concave the rigid bottom pallet is concave in shape also.

16 Claims, 10 Drawing Sheets

FLEXIBLE BARIATRIC OVERLAY

CROSS-REFERENCE TO RELATED APPLICATION

This application claims the benefit of U.S. provisional application entitled "Flexible Bariatric Overlay," filed Jul. 26, 2011, and assigned Ser. No. 61/511,574, the entire disclosure of which is hereby incorporated by reference.

BACKGROUND

1. Field of the Invention

Embodiments herein generally relate to apparatuses for assisting patient movement. In particular, the present invention relates to novel apparatuses for assisting a patient to move to/from a gurney to/from a patient handling system.

2. Description of the Related Art

When undergoing medical imaging procedures, patients often need assistance when moving to/from a patient handling system ("PHS") to/from a gurney. For example, a patient may need to remain immobile (to prevent further injury or pain), be unconscious, or is bariatric. Regular imaging systems are typically not optimized for bariatric patients. In prior art systems, patients are transferred via sheets or sliding boards. During imaging a patient is secured with straps. Currently the patient has to be transferred across gaps and surface elevation changes. In addition, bariatric patients are bigger, heavier, have more loose body mass and are potentially not ambulant. Bariatric patients often have loose skin that can get pinched during patient positioning or imaging. Wide patients have relatively little lateral support. This lack of lateral support can cause motion artifacts and/or patient rolling on the imaging table. As a result, current systems for moving bariatric patients have a series of problems (e.g., patient transfer, appropriately securing the patient, and positioning the patient during a scan).

Figure 1:
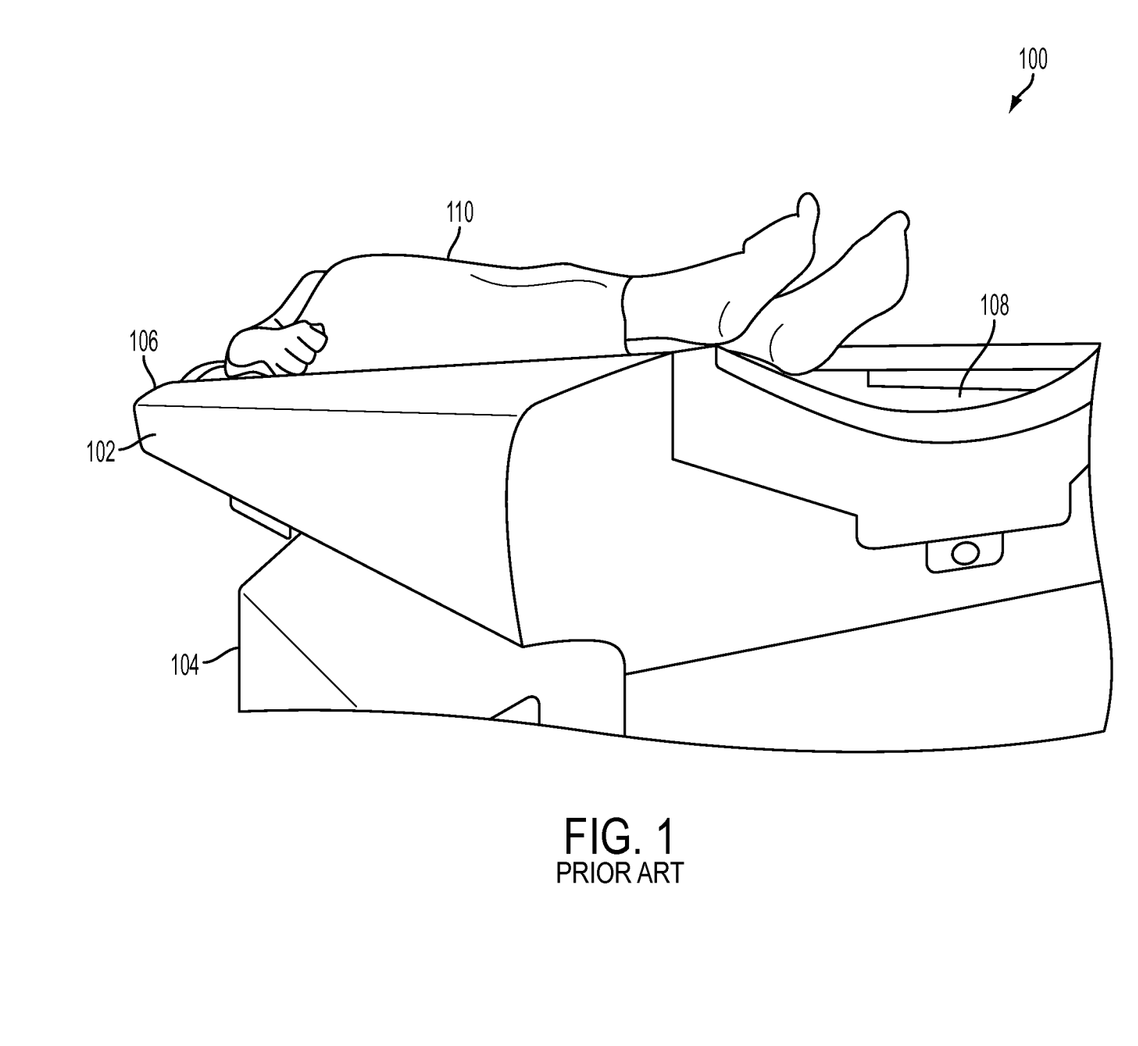
FIG. 1 depicts a patient handling system ("PHS") in accordance with the prior art.

FIG. 1 depicts a PHS 100 in accordance with the prior art. The PHS 100 includes a scanning bed 102. The scanning bed 102 includes a scanning bed support 104, a scanning bed flange 106, and a concave bed pallet 108. The scanning bed flange 106 is downwardly angled away from the scanning bed 102. The concave bed pallet 108 cradles a patient 110 lying on the scanning bed 102.

Because of elevation differences between a gurney and the PHS 100 (i.e., the concave bed pallet 108), a surface formed by the transition to/from the PHS 100 to/from the gurney can be difficult. To further complicate matters patient pads used to support the patient during transition buckle.

Therefore there is a need in the art for improved patient transfer to/from a PHS that provides a reduced surface elevation change, wider patient support, greater lateral patient support, reduced patient motion, reduced pinch hazards, and reduced danger due to a patient rolling off of the PHS and/or gurney.

SUMMARY

The present invention generally relates to novel apparatuses for assisting a patient to move to/from a gurney to/from a patient handling system. In one embodiment, a bariatric overlay is provided that includes a flexible top pallet and a rigid bottom pallet. A bladder resides between the flexible top pallet and the rigid bottom pallet. When actuated, the bladder expands and props up a central axis of the flexible top pallet. The flexible top pallet, rigid bottom pallet, and bladder are made of a material translucent to an imaging modality.

In various embodiments, the shape of the rigid bottom pallet is similar to the shape of the scanning bed of the patient handling system. For example, when the shape of the scanning bed is concave the rigid bottom pallet is concave in shape also. Thus, when the flexible top pallet is deflated the flexible top pallet is concave also.

In various embodiments, the flexible top pallet and the rigid bottom pallet include a fluid resistant cover.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

To facilitate understanding, identical reference numerals have been used, wherever possible, to designate identical elements that are common to the figures.

DETAILED DESCRIPTION

In the following description, numerous specific details are set forth to provide a more thorough understanding of the invention. As will be apparent to those skilled in the art, however, various changes using different configurations may be made without departing from the scope of the invention. In other instances, well-known features have not been described in order to avoid obscuring the invention. Thus, the invention is not considered limited to the particular illustrative embodiments shown in the specification and all such alternate embodiments are intended to be included in the scope of the appended claims.

Embodiments of the invention, as disclosed herein, can be used with various medical imaging systems.

Figure 2:
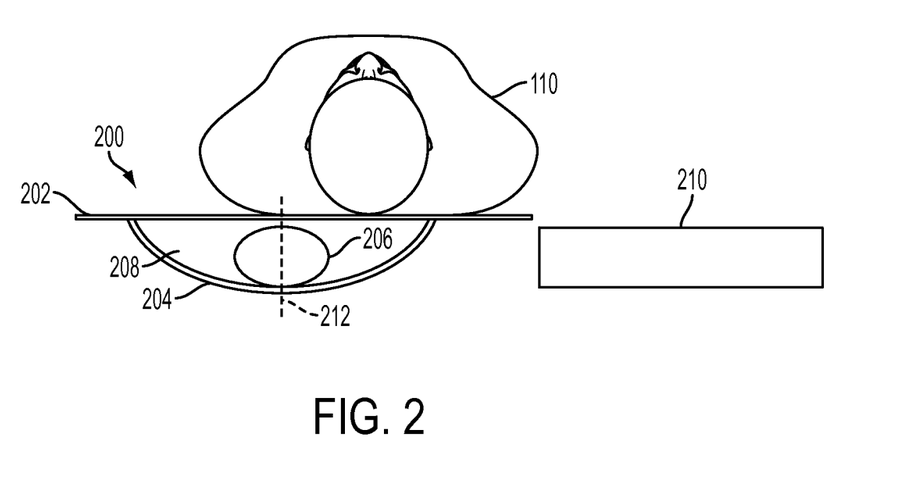
FIG. 2 depicts an embodiment of the invention, in an inflated state, in accordance with aspects disclosed herein.
Figure 4:
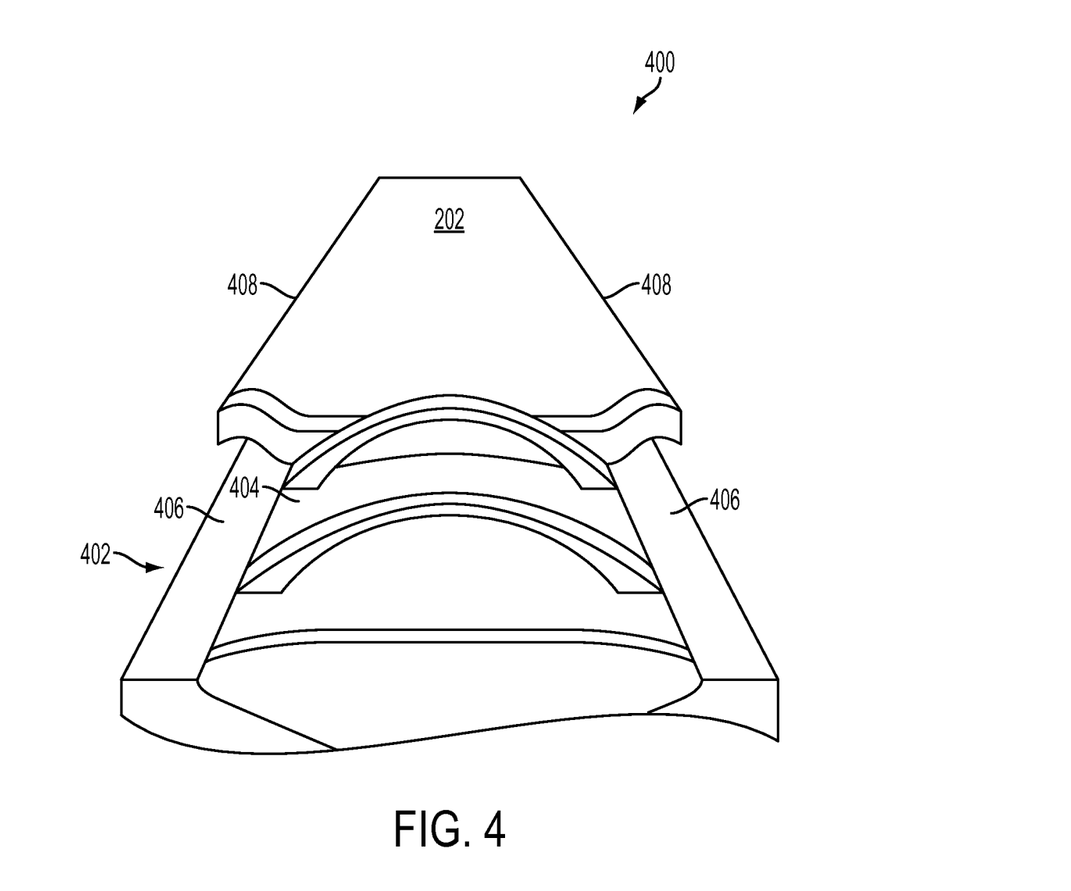
FIG. 4 depicts a perspective view of an embodiment of the invention in accordance with aspects disclosed herein.

FIG. 2 depicts an embodiment of a bariatric overlay 200 of the invention, in an inflated state, in accordance with aspects disclosed herein. Specifically, the bariatric overlay 200 includes a flexible top pallet 202 and a rigid bottom pallet 204. A bladder 206 resides in a cavity 208 formed between the flexible top pallet 202 and the rigid bottom pallet 204. The shape of the rigid bottom pallet 204 is similar to the shape of a bed pallet (not shown in FIG. 2) thereby allowing the bariatric overlay 200 to reside on the bed pallet 404 of the PHS 402 (as shown in FIG. 4 below).

For illustrative purposes only, the bed pallet 404 and rigid bottom pallet 204 (hereinafter illustratively described as "concave rigid bottom pallet 204") are described herein (and depicted in the FIGS.) as having a concave shape. However, the description (and depiction in the FIGS.) is for illustrative purposes only and not intended in any way to limit the scope of the invention. For example, in other embodiments, the bed pallet 404 and rigid bottom pallet 204 can have a shape other than concave.

FIG. 2 depicts the bariatric overlay 200 with the bladder 206 inflated. Inflation of the bladder 206 causes the flexible top pallet 202 to be propped up and to provide a flat surface. Prior to and during transfer of the patient 110, the flexible top pallet 202 is flat (due to bladder 206 inflation). While flat, the flexible top pallet 202 allows easier movement of a patient 110 to/from the bariatric overlay 200 (in the inflated state) to/from the gurney 210 because of the decrease in elevation differences and because the patient 110 does not have to be lifted off of the gurney 210 and placed into the recessed concave bed pallet 108.

The flexible top pallet 202, concave rigid bottom pallet 204, and bladder 206 can be constructed of various materials. However, the materials upon which the bariatric overlay 200 are made of should be translucent to imaging modalities. For example, in various embodiments, the flexible top pallet 202 can be constructed of a layer of foam and a layer of carbon fiber; and the concave rigid bottom pallet 204 can be constructed of plywood, carbon fiber, or a layer(s) of carbon fiber and/or a layer of plywood (e.g., a layer of carbon fiber sandwiched between two layers of plywood). In various embodiments, the flexible top pallet 202 can be made of any translucent material (or combination of materials) that will support a patient when propped up by the inflated bladder 206 and that is flexible enough to collapse along the central axis 212 to allow cradling of the patient 110. In various embodiments, the concave rigid bottom pallet 204 can be made of any translucent material (or combination of materials) that provides sufficient rigidity to maintain its shape when the patient 110 is on the bariatric overlay 200.

In addition, in various embodiments, the bariatric overlay 200 can include an outer layer of fluid impermeable material which allows protection (and cleaning) against patient fluid (s) and other substances.

The bladder 206 inflates and deflates uniformly. In various embodiments of the invention, the bladder 206 contains different chambers for uniform inflation and deflation. Inflation/deflation of the bladder 206 can occur in various ways and is not intended to limit the scope of the invention (e.g., through mechanical devices, pneumatic devices, and or oil pressure devices). In various embodiments, the bladder 206 only has a sufficient size and structural integrity to prop up the flexible top pallet 202 along the central axis 212 so that the flexible top pallet 202 is flat and supports the patient 110.

In various embodiments, the mechanism which inflates the bladder 206 is also used in another device. For example, when the bladder 206 is pneumatically inflated the device which forces air into the bladder 206 can also provide air to another device.

Figure 3:
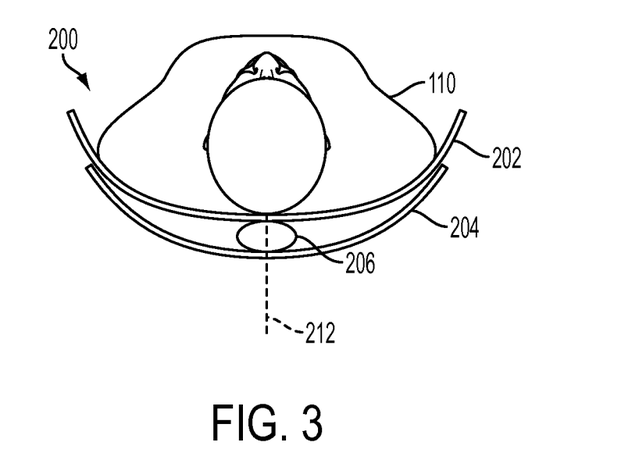
FIG. 3 depicts the embodiment of the invention depicted in FIG. 2, in a deflated state, in accordance with aspects disclosed herein.

FIG. 3 depicts an embodiment of the invention, in a deflated state, in accordance with aspects disclosed herein. Specifically, after the patient 110 is transferred to the PHS 402 (depicted in FIG. 4), the bladder 206 is deflated. Deflation of the bladder 206 reduces support provided by the bladder 206 and causes the flexible top pallet 202 to conform to the shape (e.g., concave in this embodiment) of the rigid bottom pallet 204. Deflation of the bladder 206 also allows cradling of the patient 110 due to a lack of support by the bladder 206 to the flexible top pallet 202. After examination of the patient 110, the bladder 206 is inflated to allow an easier transition of the patient 110 from the PHS 402 (not shown) to the gurney 210.

In short, the flexible top pallet 202 of the bariatric overlay 200 is flat during patient 110 transfer and concave during imaging. The bariatric overlay 200 is flexible around an axial centerline 212. During patient 110 transfer the axial centerline 212 is propped up, as described above, (e.g. with a pneumatically controlled bladder or other mechanical system). Before imaging and positioning of the patient 110 in a field-of-view ("FOV") of an imaging device 602 (depicted in FIG. 6 and described below), support of the patient 110 is gradually lowered and the flexible top pallet 202 of the bariatric overlay 200 conforms to the shape of the rigid bottom pallet. For example, when the rigid bottom pallet 204 is concave, deflation of the bladder 206 lowers the flexible top pallet 202 so that the flexible top pallet 202 is concave.

FIG. 4 depicts a perspective view 400 of an embodiment of the invention in accordance with aspects disclosed herein. Specifically, perspective view 400 depicts the bariatric overlay 200 (with an inflated bladder 206 (not shown)) and positioned on the scanning bed 404 of the PHS 402. The bladder 206 is inflated sufficiently to support the flexible top pallet 202 so that the flexible top pallet 202 lay flat. Also depicted in perspective view 400 are the flanges 406 of the scanning bed 404 and edges 408 of the flexible top pallet 202. In various embodiments, edges 408 of the flexible top pallet 202 are stiff as to provide additional lateral support to the patient 110.

Although the flanges 406 have been depicted in the figures (e.g., FIGS. 4 and 5) as having a downward slope (i.e., away from the PHS 402) those depictions are for illustrative purposes only and not intended in any way to limit the scope of the invention. For example, embodiments of the invention can be used with flanges having little or no slope, flanges that are wider or narrower than the flanges 406, and with PHS devices having no flanges.

Figure 5:
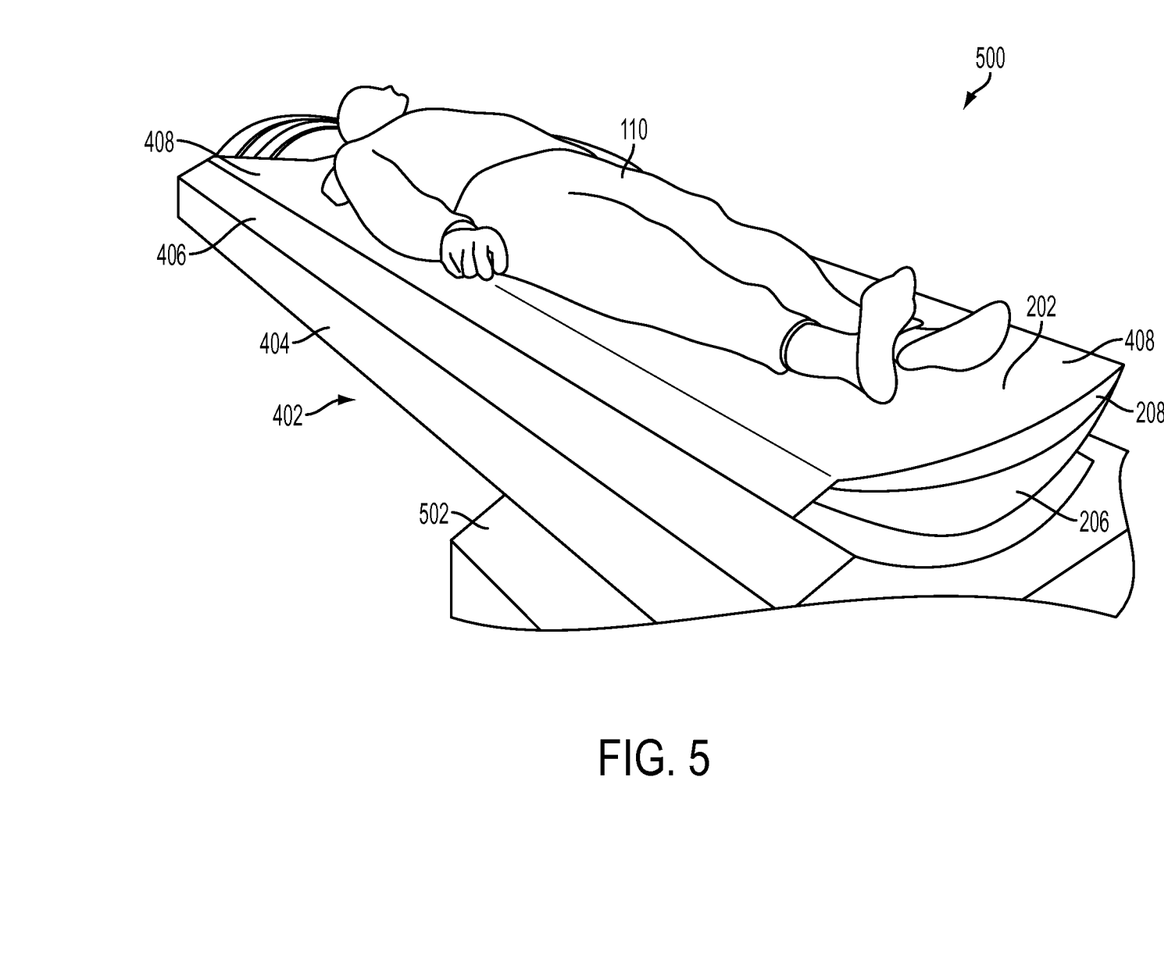
FIG. 5 depicts another perspective view of an embodiment of the invention, in accordance with aspects disclosed herein.

FIG. 5 depicts another perspective view 500 of an embodiment of the invention, in accordance with aspects disclosed herein. Specifically, perspective view 500 depicts the patient 110 lying supine on a bariatric overlay 200 (on the scanning bed 404) while the bladder 206 is inflated. Because the bladder 206 is inflated, the flexible top pallet 202 is propped up along the central axis 212, as described above, causing the flexible top pallet 202 to lay flat. FIG. 5 depicts edges 408, of the flexible top pallet 202, that help to provide structural integrity to the flexible top pallet 202 when the bladder 206 is inflated. The flanges 406 are angled downward and away from the scanning bed 404 (not shown). FIG. 5 also depicts the scanning bed support 502 supporting the PHS 402.

Figure 6:
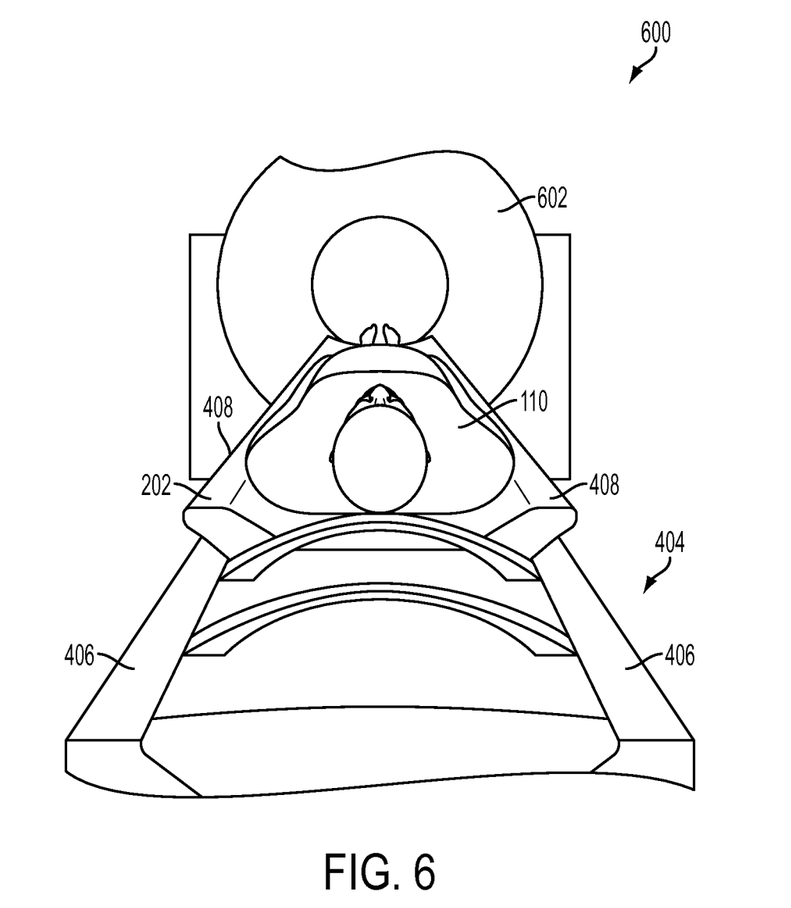
FIG. 6 depicts yet another perspective view of an embodiment of the invention in accordance with aspects disclosed herein.

FIG. 6 depicts yet another perspective view 600 of an embodiment of the invention in accordance with aspects disclosed herein. Specifically, perspective view 600 depicts the patient 110 lying supine on the bariatric overlay 200 residing on the scanning bed 404. In perspective view 600, the bladder 206 (not shown) is deflated. Because the bladder 206 is deflated, the flexible top pallet 202 is no longer propped up by the bladder 206 causing the flexible top pallet 202 to conform to the shape of the rigid bottom pallet 204 (in this embodiment the shape is concave). The concave shape of the flexible top pallet 202 cradles the patient 110 on the scanning bed 404. A gantry 602 is also depicted in FIG. 6.

Figure 7:
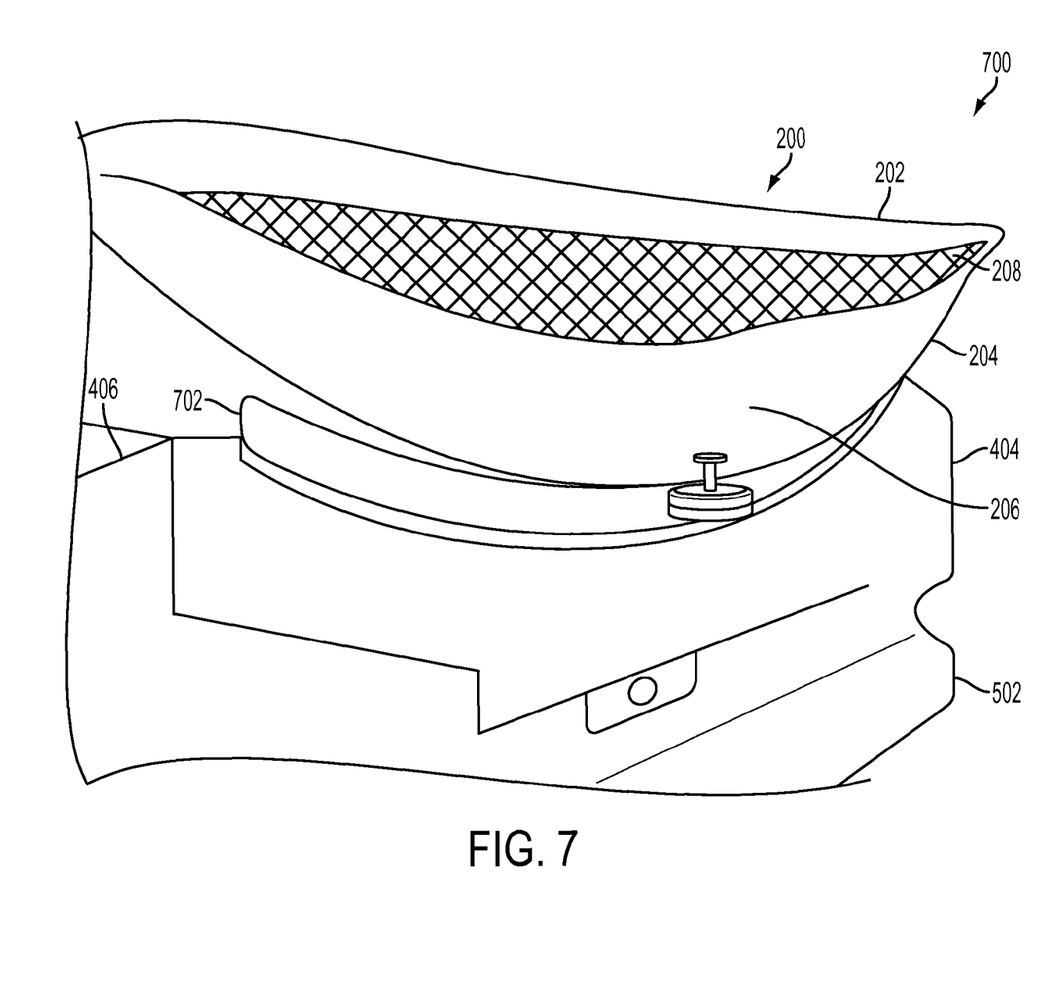
FIG. 7 depicts still another perspective view of an embodiment of the invention in accordance with aspects disclosed herein.

FIG. 7 depicts still another perspective view 700 of an embodiment of the invention in accordance with aspects disclosed herein. Specifically, perspective view 700 depicts a close up view of the bariatric overlay 200. In perspective view 700, the bladder 206 is not inflated (as evidenced by cavity 208). Also depicted in prospective view 700 is the rigid bottom pallet 204 (illustratively depicted as having a concave shape) having a concavity which allows the rigid bottom pallet 204 to reside on the bed pallet 702 (illustratively depicted and described as having a concave shape) of the scanning bed 404. The bariatric overlay 200 includes a cavity 208 that allows expansion of the bladder 206 (to an inflated state). Prospective view 700 includes flanges 406 and scanning bed support 502.

Figure 8:
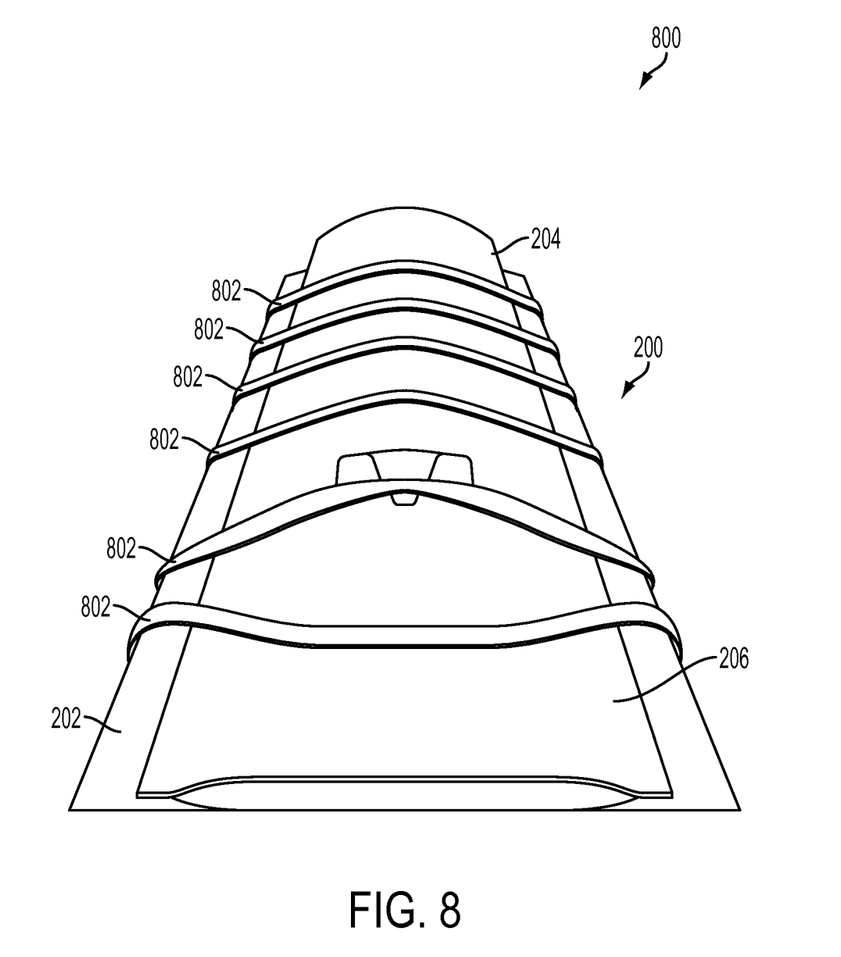
FIG. 8 depicts a bottom perspective view of an embodiment of the invention in accordance with aspects disclosed herein.

FIG. 8 depicts a bottom perspective view 800 of an embodiment of the invention in accordance with aspects disclosed herein. Specifically, bottom perspective view 800 depicts bariatric overlay 200 upside down (i.e., having the rigid bottom pallet 204 on top). Multiple straps 802 (depicted as shaded) are attached to the bottom longitudinal edges of the flexible top pallet 202. The bladder 206 (depicted as having diagonal lines) is placed between the straps 802 and the flexible top pallet 202 so that the bladder 206 is in direct contact with the flexible top pallet 202. The rigid bottom pallet 204 is also placed under the straps 802 so that the bladder 206 is between the flexible top pallet 202 and the rigid bottom pallet 204.

For illustrative purposes only, the rigid bottom pallet 204 is depicted as not under all of the straps 802. This illustration allows clearer viewing of bladder 206 between the flexible top pallet 202 and the rigid bottom pallet 204. This illustration also shows one embodiment of how the flexible top pallet 202, bladder 206, and rigid bottom pallet 204 are in contact to form the bariatric overlay 200.

Although FIG. 8 depicts the bariatric overlay 200 as utilizing multiple straps 802 that depiction is for illustrative purposes only and not intended in any way to limit the scope of the invention. In various embodiments of the invention, the flexible top pallet 202 is secured to the rigid bottom pallet 204 in ways other than by using multiple straps 802.

Figure 9:
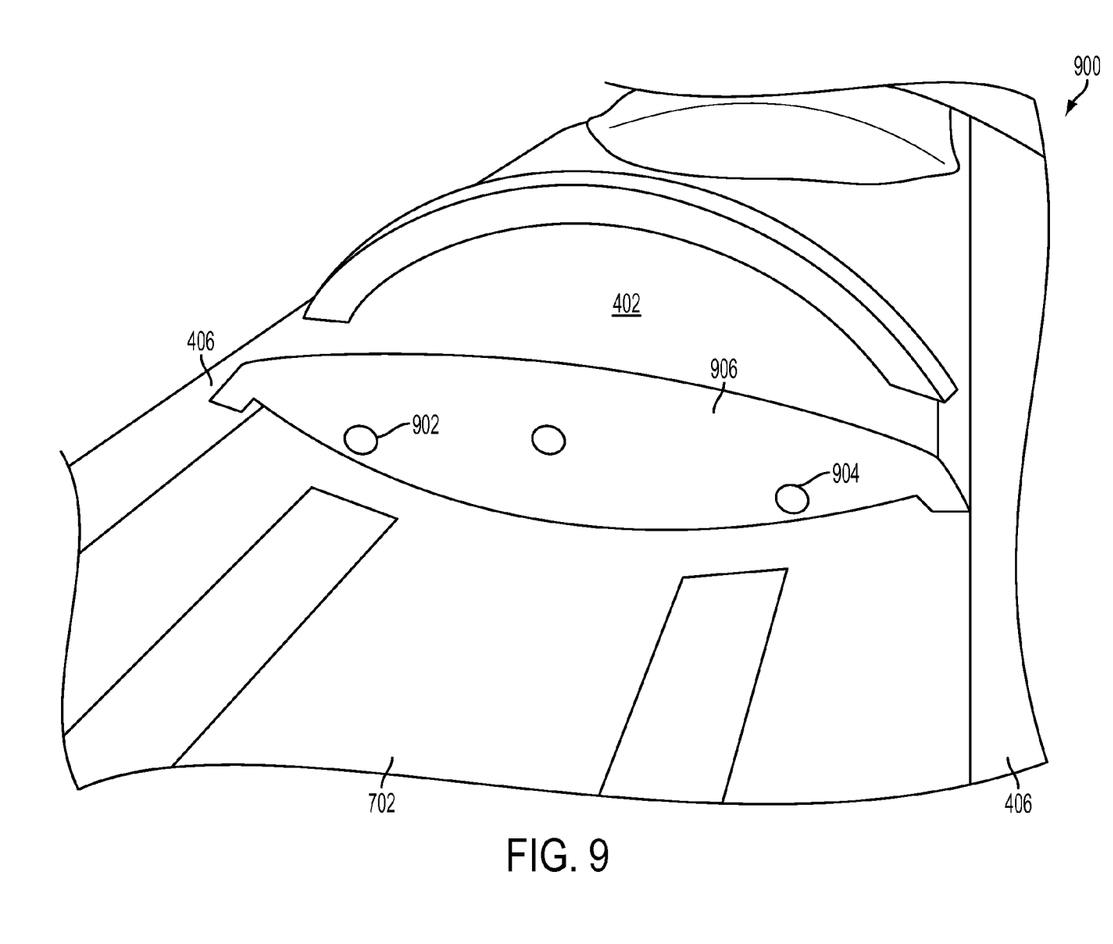
FIG. 9 depicts a perspective view of another embodiment of the invention in accordance with aspects disclosed herein.

FIG. 9 depicts a perspective view 900 of another embodiment of the invention in accordance with aspects disclosed herein. Specifically, perspective view 900 is a close-up view of the PHS 402. The bed pallet 702 (illustratively depicted and described hereinafter as "the concave bed pallet 702") has two ends (only one end 906 is depicted in FIG. 9). End 906 is substantially vertical and substantially perpendicular to the concave bed pallet 702.

End 906 includes a plurality of female portions (illustratively female members 902 and 904. Female portions 902 and 904 are adapted to receive corresponding male portions (depicted in FIG. 10 and described below) positioned on the bariatric overlay 200.

Figure 10:
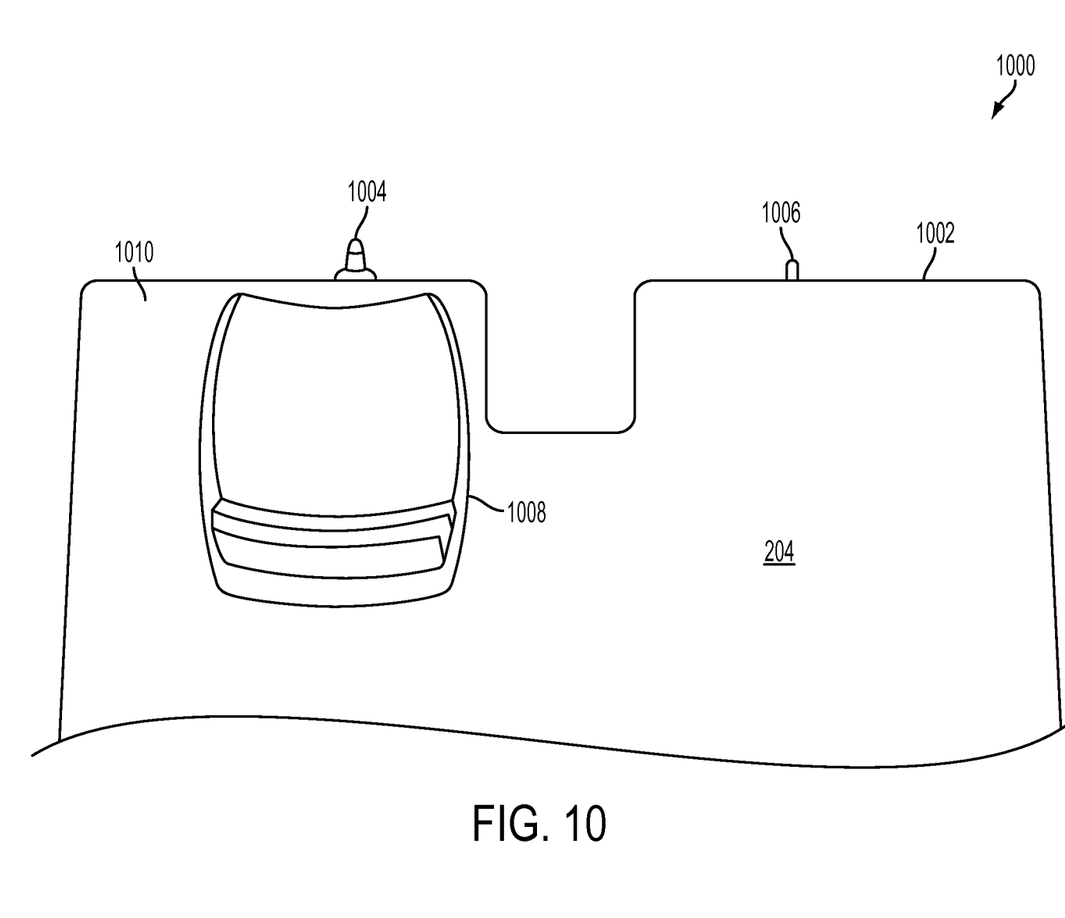
FIG. 10 depicts another perspective view of another embodiment of the invention in accordance with aspects disclosed herein.

FIG. 10 depicts another perspective view 1000 of another embodiment of the invention in accordance with aspects disclosed herein. Specifically, perspective view 1000 depicts the rigid bottom pallet 204. The rigid bottom pallet 204 has an interior surface 1010 and an exterior surface (not shown).

The exterior surface of the rigid bottom pallet 204 is in direct contact with the concave bed pallet 702 when secured to the PHS 402.

The interior surface 1010 has mounted thereon a lock mechanism 1008 that when actuated allows retractable male member 1004 to move. Also mounted on the first end 1002 of the rigid bottom pallet 204 is fixed male member 1006. The retractable male member 1004 and fixed male member 1006 are configured and positioned to mate with female member 902 and female member 904, respectively. Insertion of the retractable male member 1004 into the female member 902 and of the fixed male member 1006 into the female member 904 helps to prevent the bariatric overlay 200 from flipping over the patient 110 is being moved. Further prevention of flipping over of the bariatric overlay 200 is providing by another mechanism on an opposite end of the rigid bottom pallet 204 (depicted in FIG. 11 and described below in a description of FIG. 11).

Figure 11:
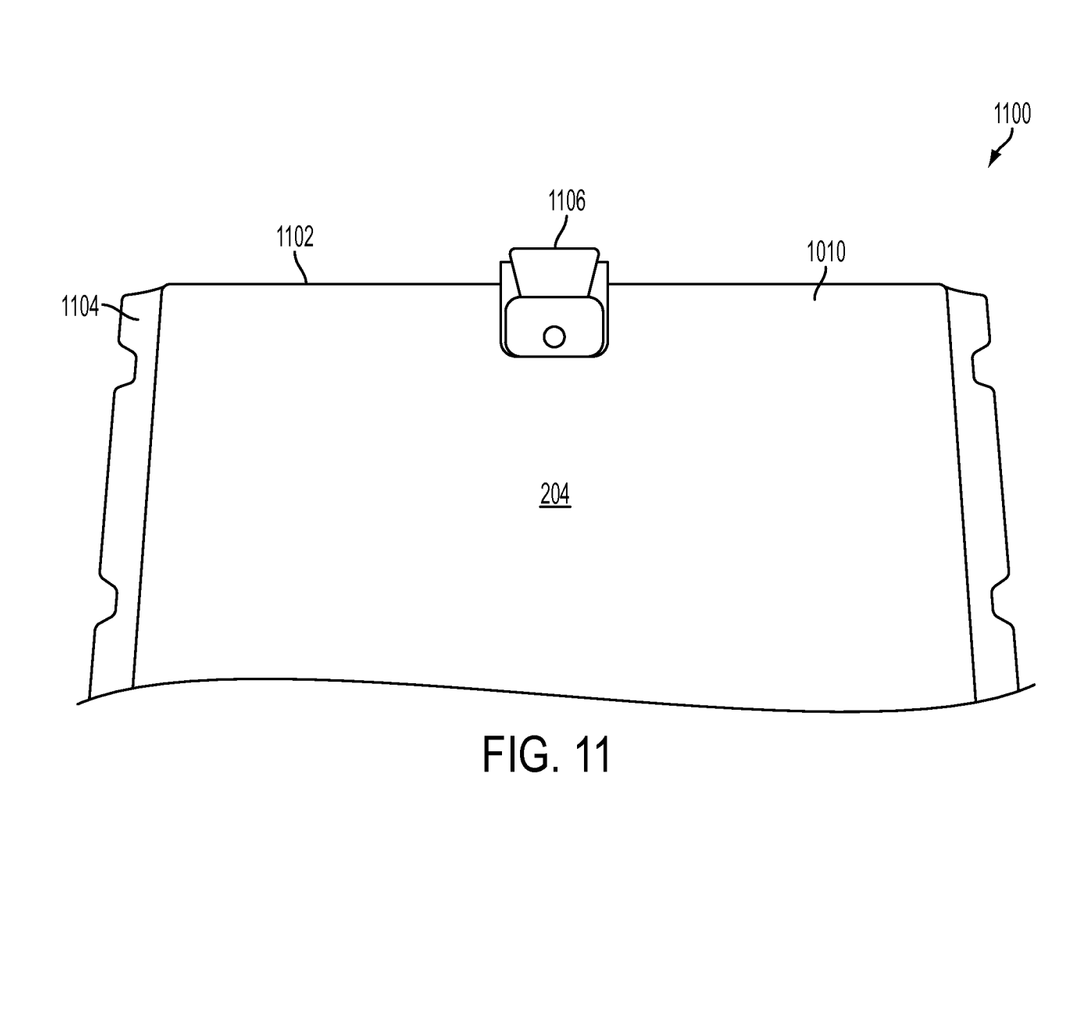
FIG. 11 depicts yet another perspective view of another embodiment of the invention in accordance with aspects disclosed herein.

FIG. 11 depicts yet another perspective view 1100 of another embodiment of the invention in accordance with aspects disclosed herein. FIG. 11 depicts a second end 1102 of rigid bottom pallet 204 having an interior surface (not shown) and an exterior surface 1010.

The exterior surface 1010 of the rigid bottom pallet 204 is in direct contact with the concave bed pallet 702 when secured to the PHS 402.

The second end 1102 includes edges 1104 and a receptacle 1106. The receptacle 1106 is positioned on the rigid bottom pallet 204 to receive a male member (not shown) located on the concave bed pallet 702 (not shown). A combination of the reception of the retractable male member 1004 by the female member 902, a reception of the fixed male member 1006 by the female member 904, and a reception of the male member (not shown) by the receptacle 1106 secures the bariatric overlay 200 and further prevents the bariatric overlay 200 from flipping over.

Various depictions in FIGS. 9, 10, and 11 are for illustrative purposes only and not intended in any way to limit the scope of the invention. For example, although FIGS. 9, 10, and 11 have been depicted as using generally located male portions (1004 and 1006), female portions (902 and 904), and a locking mechanism 1008 to secure the bariatric overlay 200 to the scanning bed 404 of the PHS 402 those depictions are not intended to limit the scope of the invention. In various embodiments, other configurations of components (e.g., mechanisms, latches, and/or "tongue and groove" combinations) can be used to secure the bariatric overlay 200 to the scanning bed 404 of the PHS 402.

While the foregoing is directed to embodiments of the present invention, other and further embodiments of the invention may be devised without departing from the basic scope thereof, and the scope thereof is determined by the claims that follow.

The invention claimed is:

1. A bariatric overlay for supporting a patient comprising:
a flexible top pallet having a first end and a second end wherein the patient is located on said flexible top pallet between said first and second ends and wherein a plurality of female portions are disposed in at least one of said first end and second end of said flexible top pallet;
a rigid bottom pallet having a first end and a second end and a plurality of retractable male members disposed on at least one of the first end and second end of said rigid bottom pallet;
a bladder located between said flexible top pallet and said rigid bottom pallet wherein inflation of said bladder raises substantially all of said flexible top pallet to change a shape of said flexible top pallet from a concave shape to a flat shape between said first and second ends of said flexible top pallet to raise the entire patient; and a locking mechanism for engaging and locking the plurality of retractable male members of said rigid bottom pallet with the plurality of female members of said flexible top pallet, wherein the engaging and locking prevents the bariatric overlay from flipping over.

2. The overlay of claim 1 wherein said rigid bottom pallet is concave and is adapted to reside on a concave scanning bed; and said concave rigid bottom pallet and said flexible top pallet having a cavity there-between.

3. The overlay of claim 1 wherein said flexible top pallet, said rigid bottom pallet, and said bladder are made of a material translucent to an imaging modality.

4. The overlay of claim 1 where said bladder is adapted for one of mechanical inflation, pneumatic inflation, and oil pressure inflation.

5. The overlay of claim 1 wherein said flexible top pallet and said rigid bottom pallet each further include a fluid resistant cover.

6. The overlay of claim 1 wherein said flexible top pallet further includes rigid edges.

7. The overlay of claim 1 wherein said flexible top pallet comprises a layer of carbon fiber.

8. The overlay of claim 1 wherein said rigid bottom pallet comprises a layer of carbon fiber sandwiched between layers of plywood.

9. A bariatric overlay for supporting a patient comprising:

a flexible top pallet wherein said flexible top pallet comprises an interior surface, an exterior surface, a first longitudinal edge, and a second longitudinal edge and wherein the patient is located between first and second ends of said flexible top pallet;

a rigid bottom pallet in contact with said interior surface of said flexible top pallet, wherein said rigid bottom pallet comprises an interior surface and an exterior surface; and a bladder located between said flexible top pallet and said rigid bottom pallet wherein inflation of said bladder raises substantially all of said flexible top pallet to change a shape of said flexible top pallet from a concave shape to a flat shape between said first and second ends of said flexible top pallet to raise the entire patient, wherein said flexible top pallet further comprises a plurality of straps, wherein each strap in said plurality of straps includes a first end and a second end attached to said interior surface of said flexible top pallet.

10. The bariatric overlay of claim 9, wherein said rigid bottom pallet is concave.

11. The overlay of claim 9 where said bladder is adapted for one of mechanical inflation, pneumatic inflation, and oil pressure inflation.

12. The overlay of claim 9 wherein said flexible top pallet, said rigid bottom pallet, and said bladder are made of a material translucent to an imaging modality.

13. The overlay of claim 9 wherein said flexible top pallet and said rigid bottom pallet each further include a fluid resistant cover.

14. The overlay of claim 9 wherein said flexible top pallet further includes rigid edges.

15. The overlay of claim 9 wherein said flexible top pallet comprises a layer of carbon fiber.

16. The overlay of claim 9 wherein said rigid bottom pallet comprises a layer of carbon fiber sandwiched between layers of plywood.

* * * * *